(12) United States Patent
Korhonen

(10) Patent No.: US 12,642,439 B2
(45) Date of Patent: Jun. 2, 2026

(54) METHOD FOR MEASURING PRE-EJECTION PERIOD

(71) Applicant: Polar Electro Oy, Kempele (FI)

(72) Inventor: Topi Korhonen, Kempele (FI)

(73) Assignee: Polar Electro Oy, Kempele (FI)

( * ) Notice: Subject to any disclaimer, the term of this patent is extended or adjusted under 35 U.S.C. 154(b) by 268 days.

(21) Appl. No.: 17/544,892

(22) Filed: Dec. 7, 2021

(65) Prior Publication Data

US 2022/0183572 A1 Jun. 16, 2022

(30) Foreign Application Priority Data

Dec. 16, 2020 (EP) ..................................... 20214499

(51) Int. Cl.
*A61B 5/02* (2006.01)
*A61B 5/00* (2006.01)
(Continued)

(52) U.S. Cl.
CPC ...... *A61B 5/02028* (2013.01); *A61B 5/02416* (2013.01); *A61B 5/02438* (2013.01);
(Continued)

(58) Field of Classification Search
CPC ............ A61B 5/02028; A61B 5/02416; A61B 5/02438; A61B 5/0245; A61B 5/1102;
(Continued)

(56) References Cited

U.S. PATENT DOCUMENTS 6,360,123 B1 * 3/2002 Kimchi ................ A61B 5/0215
324/692
2002/0062088 A1 * 5/2002 DePasquale ........... A61B 5/364
600/516
(Continued)

FOREIGN PATENT DOCUMENTS

CN 101357062 A * 2/2009

OTHER PUBLICATIONS

Averaging a curve fitting technique (Year: 2024).*
(Continued)

*Primary Examiner* — Hien N Nguyen
(74) *Attorney, Agent, or Firm* — FisherBroyles, LLP

(57) ABSTRACT
A solution for estimating a cardiac pre-ejection period is disclosed. According to an aspect, a method includes: measuring, from a user by using a plurality of cardiac sensor devices, electrocardiogram measurement data, a first set of cardiac measurement data measured at a first location of the user's body a first distance from the user's heart, and a second set of cardiac measurement data measured at a second location of the user's body a second distance from the heart, the second distance different from the first distance, wherein the electrocardiogram measurement data is clock-synchronized with the first set of cardiac measurement data and second set of cardiac measurement data; determining, in the electrocardiogram measurement data, a first set of time instants associated with electric heart activations; determining, in the first set of cardiac measurement data, a second
(Continued)

set of time instants associated with detections of blood pulses at the first location, the blood pulses resulting from the electric heart activations; determining, in the second set of cardiac measurement data, a third set of time instants associated with detections of the blood pulses at the second location; forming a set of scatter points on the basis of at least the second set of time instants and the third set of time instants and performing a fitting for the scatter points; and computing the cardiac pre-ejection period from at least one parameter describing the fitting.

12 Claims, 5 Drawing Sheets

(51) Int. Cl.
 *A61B 5/024* (2006.01)
 *A61B 5/0245* (2006.01)
 *A61B 5/11* (2006.01)
(52) U.S. Cl.
 CPC .......... *A61B 5/0245* (2013.01); *A61B 5/1102* (2013.01); *A61B 5/681* (2013.01); *A61B 5/7246* (2013.01); *A61B 5/7267* (2013.01); *A61B 5/7275* (2013.01); *A61B 5/1116* (2013.01); *A61B 5/1118* (2013.01)
(58) Field of Classification Search
 CPC ..... A61B 5/681; A61B 5/7246; A61B 5/7267; A61B 5/7275; A61B 5/1116; A61B 5/1118; A61B 5/0022; A61B 5/165; A61B 5/352; A61B 5/6804; A61B 5/6823; A61B 5/6824; A61B 5/7235; A61B 5/74; A61B 5/14551; G16H 50/20
 See application file for complete search history.

(56) References Cited

U.S. PATENT DOCUMENTS

| | | | | |
|---|---|---|---|---|
| 2014/0039330 | A1* | 2/2014 | Seo ................... | A61B 5/02255 |
| | | | | 600/509 |
| 2017/0119264 | A1* | 5/2017 | Hill ................... | A61B 5/02125 |
| 2018/0085012 | A1* | 3/2018 | Wei ........................ | G06F 21/31 |
| 2018/0303353 | A1* | 10/2018 | Baxi ................. | A61B 5/02125 |
| 2019/0254524 | A1 | 8/2019 | Granqvist et al. | |
| 2019/0274553 | A1* | 9/2019 | Peters ................... | A61B 5/022 |
| 2020/0288985 | A1 | 9/2020 | Robinson et al. | |
| 2021/0386300 | A1* | 12/2021 | Rogers .................. | A61B 5/746 |

OTHER PUBLICATIONS

Non linear curve fitting technique using averaging (Year: 2024).*
Polynomial regression a non linear curve fitting technique (Year: 2024).*
Extended European Search Report received for EP Patent Application Serial No. 20214499.4 dated Jun. 9, 2021, 3 pages.
Oreggia et al., "Physiological Parameters Measurements in a Cardiac Cycle via a Combo PPG-ECG system", Information Engineering and Mathematical Models, Oct. 14, 2015, 6 pages.
Ermishkin et al., "Variable Impedance Cardiography Waveforms: How to Evaluate the Preejection Period more Accurately", Journal of Physics, vol. 407, Dec. 20, 2012, pp. 1-6.

* cited by examiner

14: PPG SENSOR

20

10: ECG SENSOR

12: PPG SENSOR

16: BCG SENSOR

PEP $t_R$   $t_0$   $t_1$   $t_2$

TIME $S_1$ $S_2$

START

700: TRIGGER START OF EXERCISE OR TEST

702: OUTPUT USER INSTRUCTIONS TO CONDUCT TEST OR EXERCISE

302

704: NEW PHASE?    YES

NO

END

800

806

12

802

804

METHOD FOR MEASURING PRE-EJECTION PERIOD

CROSS-REFERENCE TO RELATED APPLICATION

This application claims benefit and priority to European Application No. 20214499.4, filed Dec. 16, 2020, which is incorporated by reference herein in its entirety.

BACKGROUND

Field

The present invention relates to a field of heart activity sensors and, in particular, to measuring pre-ejection period of a heart.

SUMMARY

A cardiac pre-ejection period (PEP) is the time elapsed between electrical depolarization of a ventricle of a heart and the beginning of ventricular ejection of a blood pulse. PEP represents the period of left ventricular contraction with the cardiac valves closed. The electrical depolarization of the ventricle can be observed in an electrocardiogram (ECG) via appearance of a QRS waveform in a measured ECG signal.

PEP is affected by a sympathetic nervous system and it has been observed to be linked to stress in the scientific literature, mental and physical stress. Therefore, measuring the PEP accurately would be advantageous.

The present invention is defined by the subject matter of the independent claims.

Embodiments are defined in the dependent claims.

BRIEF DESCRIPTION OF THE DRAWINGS

In the following the invention will be described in greater detail by means of preferred embodiments with reference to the accompanying drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figures 1, 2:
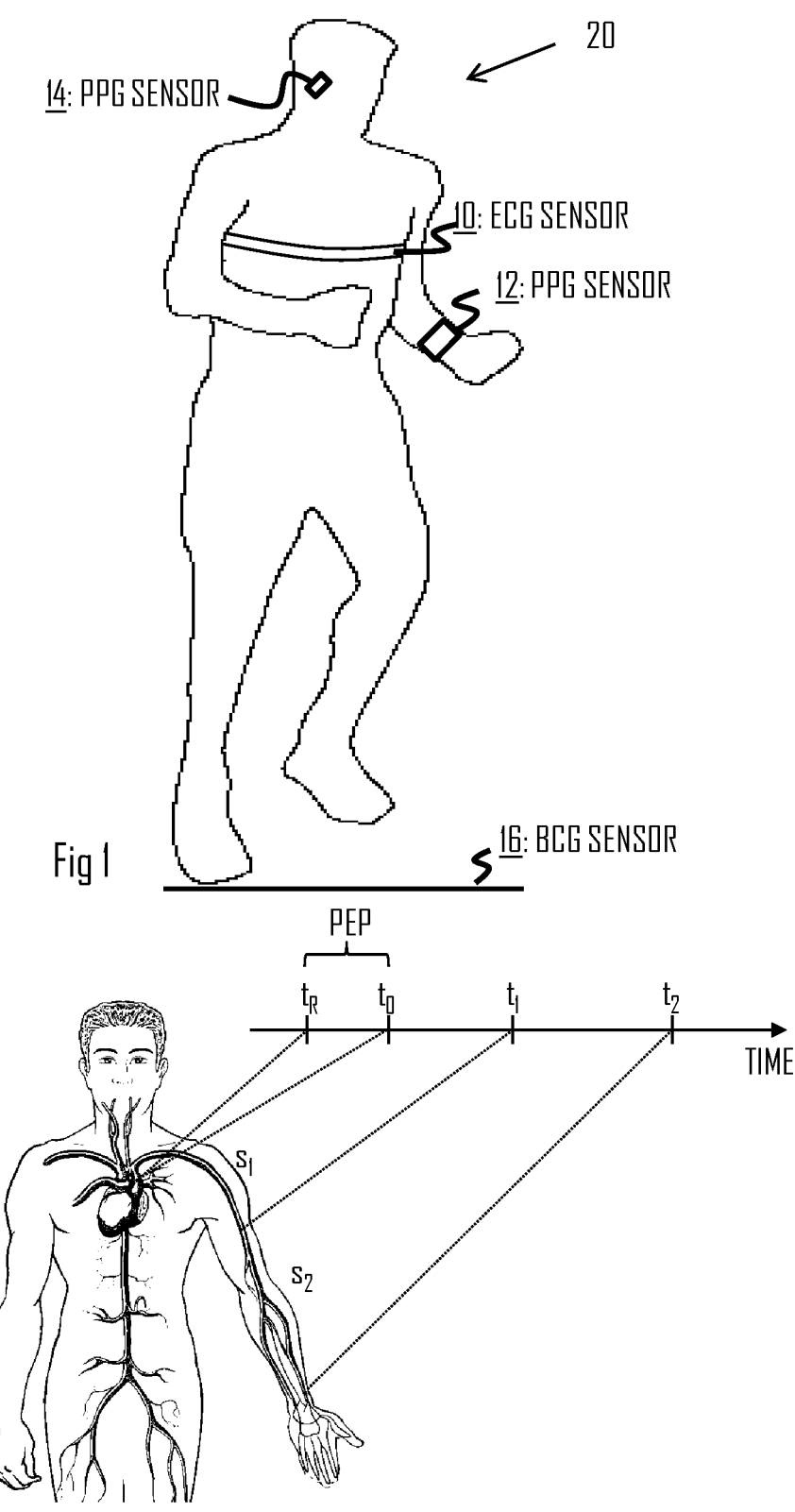
FIG. 1 illustrates a measurement arrangement to which embodiments of the invention may be applied.
FIG. 2 illustrates flow of a blood pulse.

FIG. 1 illustrates a measurement system comprising sensor devices that may be used in the context of some embodiments of the present invention. The sensors may employ one or more measurement technologies for measuring cardiac activity (heart activity) of a user 20. For example, at least one sensor device 10 may be configured to measure electrocardiogram (ECG) of the user 20. Such an ECG sensor 10 may comprise one or more electrodes arranged to be in contact with the user's 20 skin in order to measure electric charges generated during each heartbeat. The ECG sensor may be portable to enable the measurement during an outdoors physical exercise, such as running or cycling.

At least one sensor device 12, 14 may be configured to measure a photoplethysmogram (PPG) optically. PPG represents a volumetric measurement of an organ. A PPG sensor 12, 14 may comprise a light source such as a light emitting diode (LED) configured to illuminate a skin of the user 20 and, further, comprise a light-sensitive sensor such as a photodiode configured to measure changes in light reflected from the illuminated skin. With each cardiac cycle, the heart pumps blood to peripheral arteries. Even though this blood wave pulse is damped by the artery system as it propagates, it is enough to distend arteries and arterioles in the subcutaneous tissue. If the light source and the light-sensitive sensor are placed appropriately against the skin, the blood wave pulse can be detected as a change in the reflecting light measured by using the light-sensitive sensor. Each cardiac cycle appears as a peak in a measurement signal acquired through the light-sensitive sensor. The blood pulse wave may be modulated by multiple other physiological systems and, therefore, the PPG may also be used to monitor breathing, hypovolemia, and other physiological conditions. The PPG may be measured at various locations of the human body, e.g. from a wrist (sensor 12), arm, head, foot, leg, finger, ear canal or outer ear (sensor 14).

At least one sensor device 16 may be configured to measure a ballistocardiogram (BCG). The BCG is a measure of ballistic forces generated during the heartbeat. Ballistocardiogram characterizes motion of the human body resulting from the ejection of blood into the great vessels during each heartbeat. The BCG shows on a frequency range between 1 and 20 Hertz (Hz), and is caused by the mechanical movement of the heart. As the ECG and the PPG, the BCG can be recorded by using a non-invasive sensor 16 from the surface of the body. The BCG sensor 16 may be a ballistocardiographic scale configured to measure a recoil of the human body standing on the scale. The recoil is caused by the heartbeat and can be measured from the user standing on the BCG scale, e.g. by using a pressure sensor. The BCG scale may be configured to show the user's 20 heart rate as well as weight.

Another sensor device capable of monitoring cardiac activity is a camera device provided in a portable electronic device such as a mobile phone or a tablet computer. There exist some applications using the camera device to measure cardiac activity. The camera device may be directed to the user's skin during the measurements to capture images of the skin and to analyse the cardiac activity from the images. Video is a series of such images.

As described in Background, the pre-ejection period (PEP) reflects the activity of the sympathetic nervous system and is an indicator of the user's stress level (physical and/or mental). Capability of measuring the PEP accurately would improve the accuracy of the stress estimation, recovery estimation, etc. According to the embodiments described below, the PEP may be estimated by measuring the ECG and further measuring the cardiac activity capable of performing blood pulse detection at two different body parts of the user's 20 body, wherein the two body parts are at a (non-zero) distance from the heart. FIG. 2 illustrates a measurement scenario where the cardiac activity is measured with such an arrangement. The ECG may be used to detect electrical heart activation that triggers the heart to eject the blood pulse. The detection may be based on detecting an R wave and/or a QRS complex of the ECG. The detection timing is illustrated by $t_R$ in FIG. 2. The PEP later at to, the ventricular ejection of a blood pulse occurs, the aortic valves of the heart open and the heart ejects the blood pulse to the arteries. In this arrangement the further cardiac activity measurement locations are along an arterial branch in the user's hand: a first measurement location is above the elbow and a second measurement location is below the elbow (e.g. at the wrist). When the blood pulse is detected by a cardiac activity sensor at the first location, time instant $t_1$ is recorded. When the blood pulse is detected by a cardiac activity sensor at the second location, time instant $t_2$ is recorded. A distance from the heart to the first measurement location is represented by $s_1$, and a distance between the first and second measurement locations is represented by $s_2$. Now, time instants $t_R$, $t_1$ and $t_2$ are thus known but the time interval between $t_R$ and $t_0$ should be solved to find the PEP. Further relating to the notation, $v_1$ represents blood pulse propagation velocity between the aortic valve and the first measurement location and $v_2$ represents blood pulse propagation velocity between the first measurement location and the second measurement location.

Figures 3, 4:
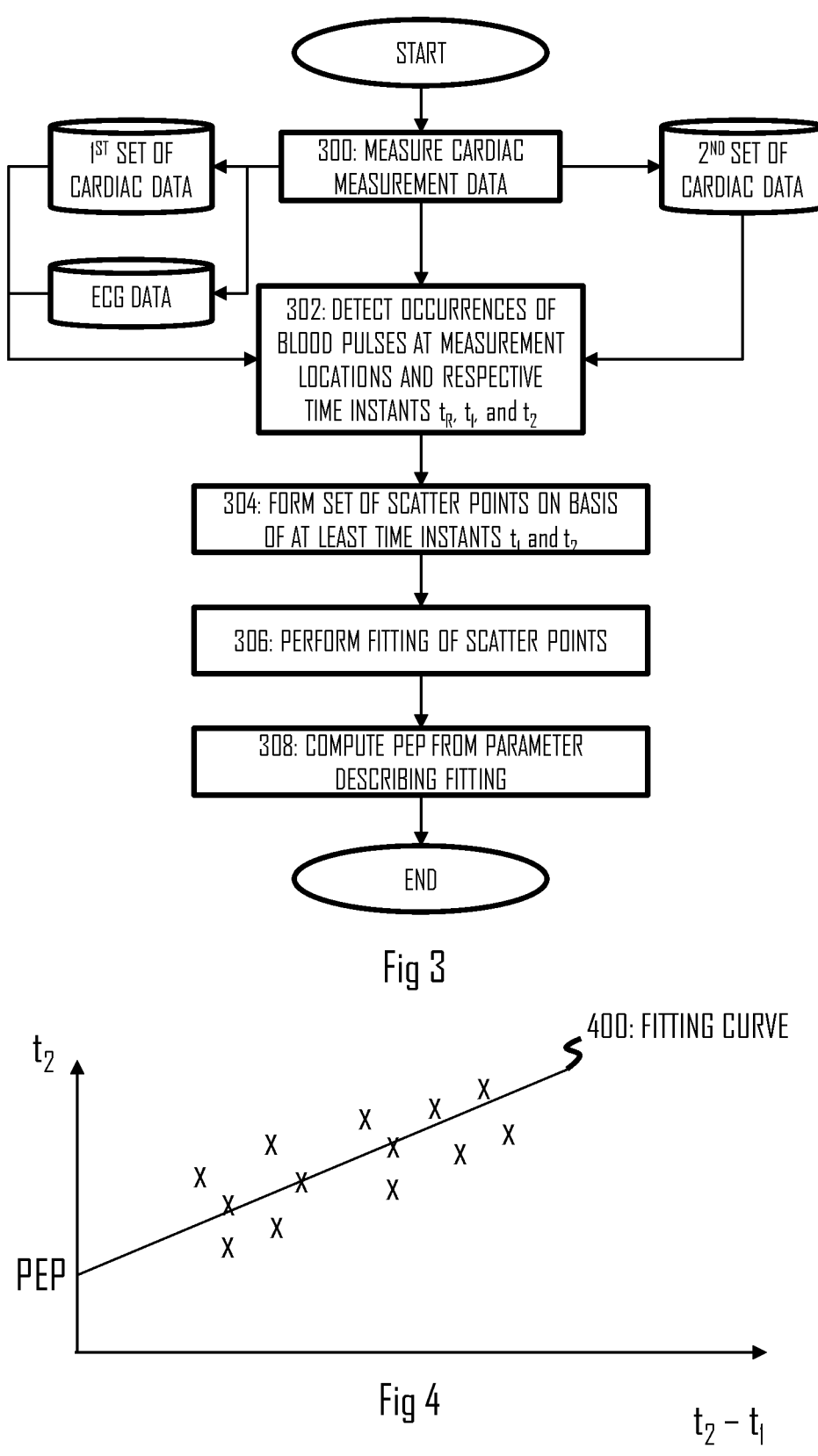
FIG. 3 illustrates a process for estimating a cardiac pre-ejection period (PEP) according to an embodiment.
FIG. 4 illustrates an embodiment of scatter points used in the process of FIG. 3.

FIG. 3 illustrates an embodiment of a process for estimating the PEP. Referring to FIG. 3, the process comprises: measuring (block 300), from the user 20 by using a plurality of cardiac sensor devices 10, 12, 14, 16, electrocardiogram, ECG, measurement data, a first set of cardiac measurement data measured at a first location of the user's body a first distance from the user's heart, and a second set of cardiac measurement data measured at a second location of the user's body a second distance from the heart, the second distance different from the first distance, wherein the ECG measurement data is clock-synchronized with the first set of cardiac measurement data and second set of cardiac measurement data; determining (block 302), in the ECG measurement data, a first set of time instants associated with electric heart activations; determining (block 302), in the first set of cardiac measurement data, a second set of time instants associated with detections of blood pulses at the first location, the blood pulses resulting from the electric heart activations; determining (block 302), in the second set of cardiac measurement data, a third set of time instants associated with detections of the blood pulses at the second location; forming (block 304) a set of scatter points on the basis of at least the second set of time instants and the third set of time instants and performing (block 306) a fitting for the scatter points; and computing (block 308) the cardiac pre-ejection period from at least one parameter describing the fitting.

The ECG measurement data, the first set of cardiac measurement data, and the second set of cardiac measurement data may be stored in respective records in a memory or in a database in block 300, and retrieved from the memory or database in block 302, as illustrated in FIG. 3.

Let us then briefly discuss the clock synchronization. When the cardiac measurements are carried out by sensors comprised in the same device or the same casing, the measurements may be synchronized by synchronizing the measurements to the same clock signal provided by a clock signal generator of the device. When the measurements are carried out by physically separated sensor devices, e.g. the ECG sensor 10 and the PPG sensor 12, the two devices may be synchronized to a common clock through other means. Literature teaches several methods for clock-synchronization of sensor devices. Some methods rely on one of the devices operating as a master clock and transmitting its clock value to the other device(s). Another option is to use an external master clock, e.g. a GPS clock.

FIG. 4 illustrates an embodiment of the scatter points formed in block 304. As illustrated in FIG. 4, the scatter points are provided in coordinates where the X axis is formed by a time difference $t_1-t_2$ and Y axis is formed by $t_2$. Accordingly, the coordinates define $t_2$ as a function of $t_1-t_2$. Let us next elaborate mathematics beyond the scatter plotting of FIG. 4. Let us make an assumption that $t_R=0$ and $PEP=t_0-t_R=t_0$. As a consequence, we can define $t_2$ as follows:

$$t_2 = PEP + \frac{s_1}{v_1} + \frac{s_2}{v_2}$$

$v_1$ and $v_2$ depend on the elasticity of veins and from the blood pressure. Let us assume that within small changes in elasticity and blood pressure $v_1$ and $v_2$ have a linear relation to each other, i.e. if $v_2$ responds to the change in $v_1$ in linear manner. This assumption enables defining the middle term in the Equation above as follows:

$$\frac{s_1}{v_1} = \frac{s_1}{kv_2} = \frac{s_1'}{v_2}$$

where $s'_1=s_1/k$ and $k$ is a coefficient describing the linear relation. $v_2$ may be defined by using the distance between the measurement points and the time difference $t_1-t_2$ as follows:

$$v_2 = \frac{s_2}{(t_2 - t_1)}$$

With the help of these definitions, $t_2$ can be rewritten as $$t_2 = PEP + \frac{s_1'}{v_2} + \frac{s_2}{v_2} = PEP + \frac{s_1'}{s_2}(t_2 - t_1) + (t_2 - t_1)$$

and derive the following function $$t_2 = \left(\frac{s_1'}{s_2} + 1\right)(t_2 - t_1) + PEP$$

This form illustrates the $t_2$ as a function of $t_2-t_1$ and defines basically an equation to a linear function in the coordinates of FIG. 4. In other words, the Equation is in the form of $y=ax+b$ where the constant term b is the PEP. Accordingly, in an embodiment the scatter points are provided as a function of a time difference between time instants of the second set and time instants of the third set that are associated with the same heart activation, and the parameter in block 308 is a value of the fitting at a point where the time difference is zero, i.e. where the function crosses the $t_2$ axis.

As seen from the function above, the PEP is the constant term of the function represented by the fitting.

A similar function may be derived in a for $t_1$, and $t_1$ can be represented as follows:

$$t_1 = \frac{\frac{s_1'}{s_2}}{\frac{s_1'}{s_2} + 1} t_2 + \frac{PEP}{\frac{s_1'}{s_2} + 1}$$

Accordingly, $t_1$ can be defined as a function of $t_2$, and we get again an Equation with the PEP in the constant part of the Equation. Similar scatter points may again be acquired, now in the coordinates where $t_1$ is on the Y axis and $t_2$ on the X axis. The fitting may again be performed and the value of the constant parameter b may be acquired, i.e. the value of $$\frac{PEP}{\frac{s_1'}{s_2} + 1}.$$

Now, if the fitting is linear, we can compute a slope value sl of the fitting, thus acquiring the value for the parameter $$\frac{\frac{s_1'}{s_2}}{\frac{s_1'}{s_2} + 1}$$

of the above Equation. This helps in computing the PEP without using the distances s. Now, the PEP may be computed as $$PEP = b\left(\frac{sl}{(sl-1)} + 1\right)$$

In an embodiment, the first measurement location and the second measurement location are along the same arterial branch of the user, e.g. along the same arm or foot, or head.

In an embodiment, the fitting is linear fitting or linear regression as illustrated by a fitting curve 400 in FIG. 4. Ordinary least squares fitting method may be used, but equally any other fitting method known in the art. In another embodiment, a non-linear fitting or non-linear regression is employed, e.g. a parabola function, where the PEP again represents the constant parameter.

In an embodiment, the PEP is computed by extrapolating the fitting curve represented by a fitted sample set towards the point where $t_2-t_{1=0}$, thus providing the constant parameter (PEP). As described above, the fitting curve 400 represents $t_2$ as the function of $t_2-t_1$. One can visualize the fitting curve such that $t_2-t_1$ reduces as the measurement points are moved towards each other and towards the heart, and $t_2-t_1=0$ at the aortic valve, resulting in $t_2=t_0=PEP$.

As an alternative to the fitting curve, a pattern analysis may be applied to the scatter points in order to derive the PEP. One or more parameters describing the scatter points may be computed on the basis of the scatter point values. Further, a look-up table may store, in connection with each parameter value or a set of parameter values, a PEP value. The parameter value(s) may be derivative(s) of the values of the scatter points and describe the pattern of the scatter points, e.g. a mathematical slope value or another parameter describing pattern and/or deviation, variance, and/or density of the scatter points. Upon computing the one or more parameter values, the look-up table may be sought for a PEP providing the best match with the one or more parameter values. Such a PEP may then be selected.

In yet another embodiment, a machine learning algorithm adapted to pattern recognition may be used to analyse the pattern formed by the scatter points and to derive the PEP on the basis of the analysis. Accordingly, the fitting in block 306 and the computation of the PEP in block 308 may be carried out in various manners.

In general, the fitting may be understood as a function analysing the measured parameter values and reproducing a desired output with given input data represented by the measured parameter values. Above, linear and non-linear fitting methods have been described. In the linear fitting or linear regression, the reproduced (fitted) model depends linearly on the measured parameters. In the non-linear fitting, the dependence is non-linear. In the fitting, the measured parameters are used to adjust the reproduced (regression) model so that the model would match better with given the measurements. The fitting maybe done by analytically calculating the optimal parameter combination defining the reproduced model, e.g. least-square fitting in linear fitting, or the fitting process may be processed with a more intelligent algorithm that iterates the reproduced model towards a descending gradient of error with the measurements.

Fitting with the machine learning may include training of a machine learning model used. Some machine learning algorithms such as a neural network may be trained by using a given input and a desired output that shall be reached with the input. In this case, the PEP may be measured via other means accurately, and respective values for $t_1$ and $t_2$ or a set of scatter points $t_1$ and $t_2$ or a value derived from $t_1$ and $t_2$ (e.g. $t_2-t_1$) may also be measured. The PEP may then be applied to an output layer of the neural network while the values of $t_1$ and $t_2$ and/or the value(s) derived therefrom may be applied to an input layer of the neural network. Then, the neural network may be arranged to find a suitable neural network structure that maps the input layer to the output layer. The training may be performed for various values of the input layer and respective desired values of the PEP in the output layer, thus training the neural network to infer the PEP on the basis of the measurements of $t_1$ and $t_2$. After the training, the measured $t_1$ and $t_2$ and the neural network may be used to determine the PEP. Other machine learning methods may use different training. For example, reinforced learning is based on providing positive or negative rewards on the basis of how accurate the PEP estimate was. The reinforced learning model may similarly be trained with the known inputs and known outputs to find the PEP on the basis of the measured values of $t_1$ and $t_2$.

Accordingly, the invention may be generalized to a method, an apparatus, or a system that computes the PEP on the basis of the pulse transit time measurements. The process of FIG. 3 may thus be generalized into a form where blocks 300 and 302 may be carried out in the above-described manner. However, blocks 304 to 308 may be replaced by computing the PEP on the basis of the time instants detected in block 302. As described above, the time instants may be input to the machine learning trained to find the PEP on the basis of the training and the received input. In another embodiment, the set of scatter points is made as described herein, and they can be processed according to any embodiment described herein.

As described above, the cardiac activity sensors may include any one of the above-described sensors. The ECG sensor is used to detect the electric heart activations but the first set of cardiac measurement data and the second set of cardiac measurement data may be measured by using a PPG sensor or a BCG sensor. The first and second set of cardiac measurement data may both be measured by using the PPG sensors or BCG sensors, or the first set of cardiac measurement data may be measured by one of the PPG sensor and the BCG sensor, and the second cardiac measurement data may be measured by the other of the PPG sensor and the BCG sensor. What matters is that the blood pulses are detected at the first and second measurement locations and that the detections are synchronized in some manner to ensure that the detections relate to the same blood pulse.

Figure 5:
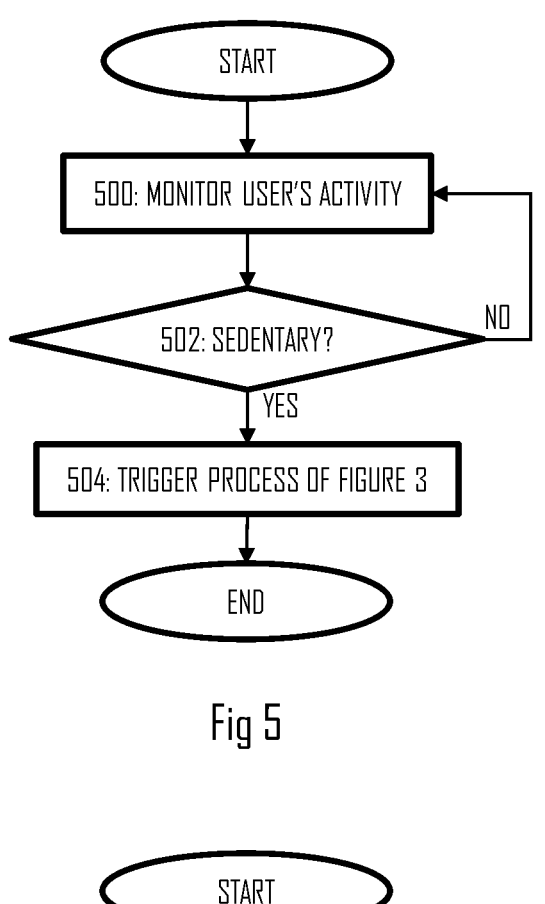
FIGS. 5 and 6 illustrate embodiments for detecting conditions suitable for PEP estimation.

The measurements may be conducted under a situation where the PEP is substantially constant. Some embodiments described in connection with FIGS. 5 to 7 enable such measurements. In an embodiment, the apparatus controlling the measurements or estimating the PEP is configured to detect a time interval where the user is sedentary and to limit the ECG measurement data and the first and second set of cardiac measurement data to include only measurement data acquired during the time interval. FIG. 5 illustrates an embodiment where the user's activity is monitored in block 500. The monitoring may include monitoring the user's motion by using a motion sensor comprising at least one of an accelerometer, gyroscope, and a magnetometer, or a similar motion sensor. The monitoring may alternatively include analysis of the cardiac measurement data, e.g. a pulse rate. If the motion sensing and/or the cardiac measurement data indicates in block 502 that the user is sedentary (no motion, stable pulse rate, etc.), the process may proceed to block 504 where the PEP estimation of FIG. 3 (or its embodiment) is triggered. Otherwise, the process may return to monitoring for the instant when the user is sedentary. In this embodiment, the PEP estimation is triggered and started when the user has been detected to be sedentary, e.g. for a determined duration. The sedentary may refer to the user lying still, sitting, standing still, sleeping, resting, etc.

Figure 6:
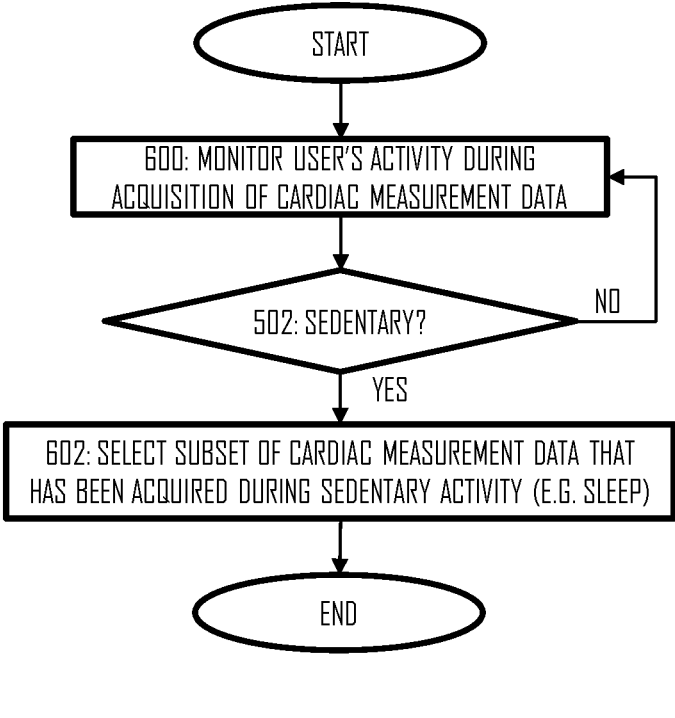

FIG. 6 illustrates an embodiment where the cardiac measurement data is measured and stored. The user's activity during the acquisition of the cardiac measurement data (ECG and first and second sets) in block 600. As described above, the monitoring may be performed by using the motion sensor and/or by analysing the cardiac measurement data. The cardiac measurement data may be labelled to include cardiac measurement data acquired while the user has been sedentary and cardiac measurement data acquired while the user has not been sedentary. In block 602, cardiac measurement data for the process of FIG. 3 (or its embodiment) is selected. The selected cardiac measurement data may include only measurement data labelled to have been measured while the user has been sedentary. In other words, the cardiac measurement data labelled to have been measured while the user has not been sedentary may be excluded from the process.

In an embodiment, the number of scatter points is at least two. Noise cancellation and/or averaging may be applied to measurement data and, accordingly, even two measurement points may be sufficient for the fitting. In other embodiments, the number of scatter points is substantially higher than two, e.g. over ten, over 50, or over 100. Then, the fitting may handle at least some of the noise cancellation or averaging.

In order to get the sufficient scattering to the scatter points, the measurements may be performed under the conditions where the pulse wave velocity (and consequently pulse transit time) changes. Breathing (or respiratory rate) as such has been observed to modulate the pulse wave velocity. A breathing exercise is an example of conditions where the user is sedentary, the PEP is substantially constant, and where the pulse wave velocity is modulated by the breathing such that sufficient scattering for the points of FIG. 4 is achieved.

Figure 7:
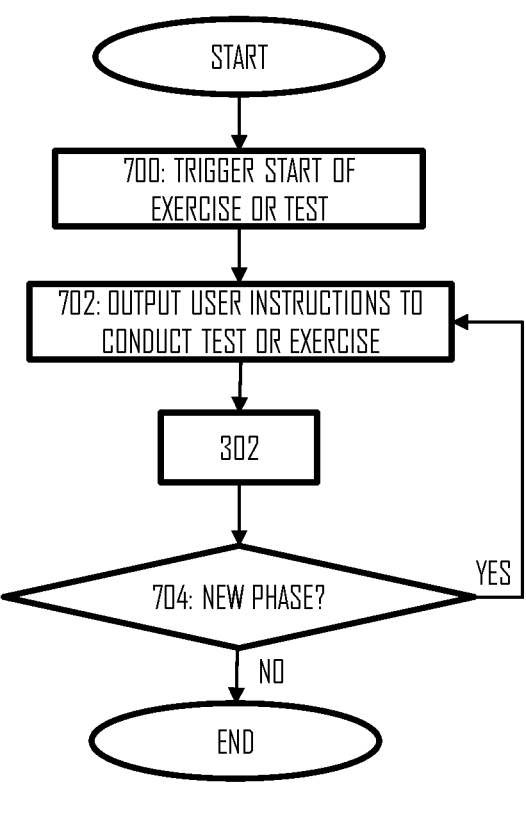
FIG. 7 illustrates a process for instructing a user in connection with measuring cardiac measurement data for the PEP estimation according to an embodiment.

FIG. 7 illustrates a procedure where the wherein a device conducting acquisition of the measurement data instructs the user to carry out an exercise or a test where the cardiac measurement data may be acquired under the suitable conditions. The procedure may be performed by a wearable device worn by the user, e.g. a wrist computer. A mobile phone may be understood as such a wearable device if the mobile phone is attached to the user's body in some manner, e.g. with a strap or a case.

In an embodiment, the procedure of FIG. 7 instructs the user to conduct a breathing exercise. In such an embodiment, the procedure comprises triggering (block 700) start of the breathing exercise and measuring (block 302) all the ECG measurement data and the first and second set of cardiac measurement data during the breathing exercise. In block 702, the user may be instructed to conduct the breathing exercise. Block 702 may include outputting instructions to conduct a certain breathing pattern or rhythm. Blocks 702 and 302 may be performed concurrently.

In an embodiment, the procedure is a fitness test where the user's heart rate variability is measured while the user is instructed to lie still. The same measurement data used for the heart rate variability estimation may be used for PEP estimation, e.g. the ECG measurement data, and further cardiac measurement data may be measured for the PEP estimation, e.g. the first and second sets of cardiac measurement data. The procedure may follow the procedure of the breathing exercise: upon triggering the fitness test in block 700, the user may be instructed to stay still (block 702) while the cardiac measurements are performed (block 302).

In an embodiment, the cardiac measurements are performed in connection with a test or an exercise comprising multiple phases where the user is instructed to be sedentary during the phases. An example of such a test is an orthostatic test or a body composition test. An example of such an exercise is a yoga exercise or a resting period in a fitness exercise such as strength training. In such an embodiment, the start of the test or exercise is triggered in block 700, as described above. In block 702, the user is instructed to perform a first phase of the test or exercise and stay still. Meanwhile, a first subset of the ECG measurement data, a first subset of the first set of cardiac measurement, and a first subset of the second set of cardiac measurement data is measured in block 302. Thereafter, it is determined that the test or exercise proceeds to the next phase where new cardiac measurements are performed (yes in block 704). Then, the process returns to block 702 where new instructions are output to the user to conduct a second phase different from the first phase and again stay still. While the user is instructed to stay still in the second phase, a second subset of the ECG measurement data, a second subset of the first set of cardiac measurement, and a second subset of the second set of cardiac measurement data is measured (block 302). In this manner further phases and further subsets of the measurement data is acquired for blocks 302 to 308 of FIG. 3.

In the embodiment where the test is the orthostatic test, the user is instructed to take multiple postures, one posture per above-described phase. One of the postures may be lying or sitting and one of the postures may be standing still. This embodiment may be used to provide one measurement point for the set of scatter points in one posture and another measurement point for the set of scatter points in another posture. The measurement point may be acquired by averaging measurement samples. Then, the fitting may be made for the two points to compute the PEP. When the number of postures is higher than two, a measurement point per posture may be acquired for the fitting.

As described above, the PEP may be used to compute at least one metric indicating a stress level of the user and the at least one metric may be output via a user interface or via a communication network. The at least one metric may indicate the user's mental stress level and/or physical stress level. The at least one metric may be used to compute a recovery estimate to the user, e.g. a recovery time. When the PEP is computed in connection with an exercise such as a fitness exercise, the PEP may be computed for the purpose of determining a physical exertion of the exercise so far. The PEP may thus be used as an input for determining whether or not the user has reached a training target in the exercise. When the PEP is computed in connection with an exercise such as a relaxation exercise, e.g. a yoga exercise, the PEP may be computed for the purpose of determining physical and/or mental relaxation of the user during the exercise. The PEP may thus be used as an input for determining whether or not the user has reached a recovery or relaxation target of the exercise. In other embodiments, the PEP is used to improve accuracy of another parameter, e.g. a pulse transit time or a heart stroke volume. For example, for the estimation of the stroke volume information on a time interval when aortic valves are open may be needed. As described above, the PEP indicates precisely the time when the aortic valves open and, accordingly, the PEP according to any embodiment described herein may be used in the stroke volume estimation.

According to an embodiment, there is provided a system for estimating the PEP. The system may comprise an ECG sensor configured to measure the ECG measurement data, a first cardiac sensor configured to measure a first set of cardiac measurement data from a first location of the user's body a first distance from the user's heart, and a second cardiac sensor configured to measure a second set of cardiac measurement data from a second location of the user's body a second distance from the heart, the second distance different from the first distance. The system may also comprise means for synchronizing the ECG measurement data with the first set of cardiac measurement data and second set of cardiac measurement data. The system may further comprise a processing system configured to carry out the procedure of FIG. 3: determine, in the ECG measurement data, a first set of time instants associated with heart activations; determine, in the first set of cardiac measurement data, a second set of time instants associated with detections of blood pulses at the first location, the blood pulses resulting from the heart activations; determine, in the second set of cardiac measurement data, a third set of time instants associated with detections of the blood pulses at the second location; form a set of scatter points on the basis of at least the second set of time instants and the third set of time instants and performing a fitting for the scatter points; and compute the cardiac pre-ejection period from at least one parameter describing the fitting.

Figure 8:
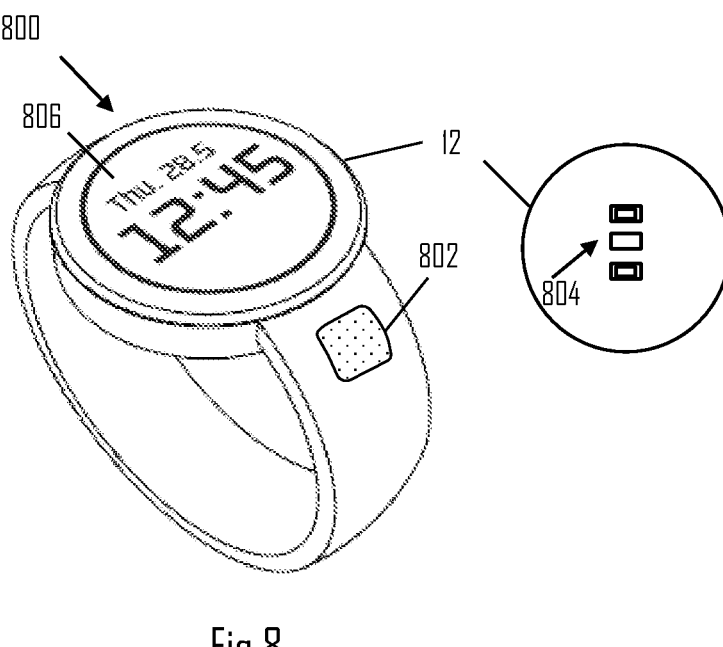
FIG. 8 illustrates an embodiment of a training computer comprising multiple sensors used for PEP estimation.

In an embodiment, the first cardiac sensor and second cardiac sensor are comprised in or attached to one or more wearable devices, and wherein the ECG sensor and at least one of the first cardiac sensor and second cardiac sensor are comprised in or attached to the same wearable device. In an embodiment, the ECG sensor, the first cardiac sensor and second cardiac sensor are comprised in or attached to the same garment, the garment and the locations of the first cardiac sensor and the second cardiac sensor defining the first location and second location, respectively. An example of such a garment is a shirt with dedicated locations for the cardiac activity sensors in a sleeve, for example. ECG electrodes may be integrated into the garment. In another embodiment, the ECG sensor and at least one of the first cardiac sensor and second cardiac sensor are comprised in a wrist-worn training computer. FIG. 8 illustrates such a training computer 800. A sensor head 804 of the first cardiac sensor (e.g. a PPG sensor 12) is provided on a face of the training computer that faces the wrist, and the ECG sensor 802 is provided on a face of the training computer not facing the wrist. The ECG sensor may be arranged in a strap, as illustrated in FIG. 8, or it may be arranged on a display screen 806 of the training computer. In the latter embodiment, the electrode(s) of the ECG sensor may be optically transparent.

In another embodiment, the garment (or an apparel) for at least one of the cardiac activity sensors is a strap, vest, headband, hearable, ring. In other embodiments, at least one of the cardiac activity sensors is provided in an object that is not worn by the user, e.g. a steering wheel or a handlebar. The ECG may be measured from any body part in the user's body.

Figure 9:
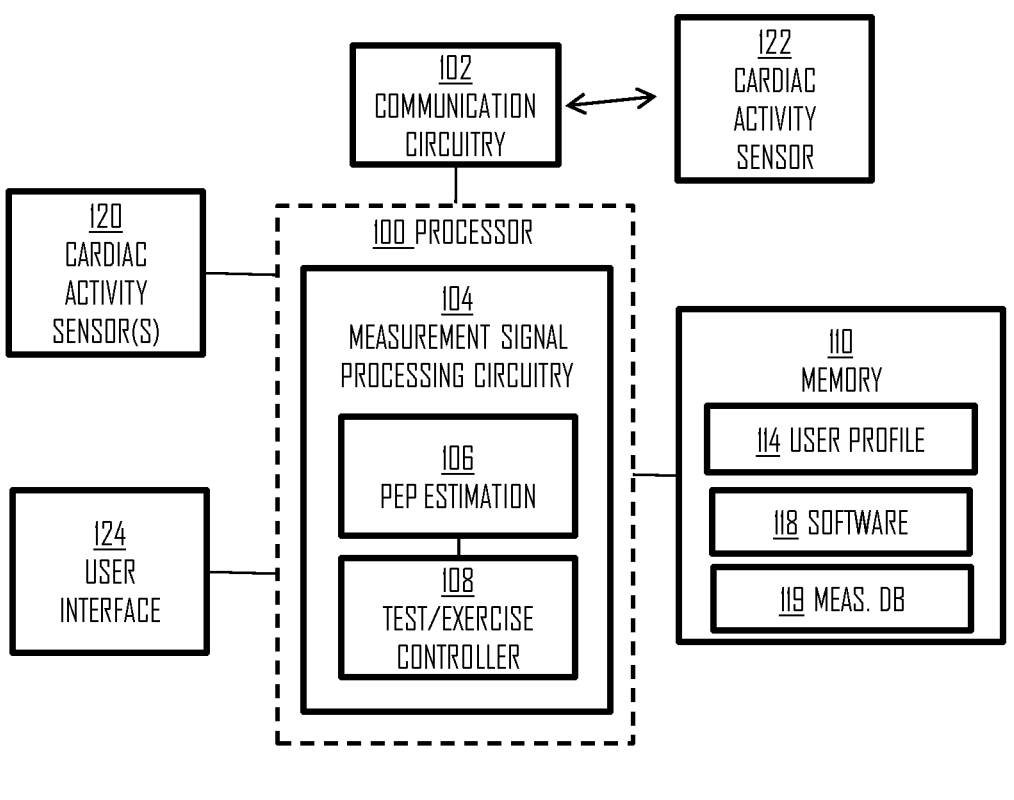
FIG. 9 illustrates an embodiment of an apparatus or a system for the PEP estimation.

FIG. 9 illustrates an embodiment of an apparatus or apparatuses (a system) configured to carry out at least some of the above-described functions in estimating the PEP. The apparatus may comprise an electronic device comprising at least one processor 100 and at least one memory 110. The processor 100 may form or be a part of a processing circuitry. The apparatus may further comprise a user interface 124 comprising a display screen or another display unit, an input device such as one or more buttons and/or a touch-sensitive surface, and an audio output device such as a loudspeaker. In some embodiments, the user interface 124 comprises a haptic output device configured to provide haptic indications to the user 20.

The processor 100 may comprise a measurement signal processing circuitry 104 configured to estimate the PEP by carrying out the procedure of FIG. 3. The measurement signal processing circuitry 104 may comprise a PEP estimation circuitry 106 configured to estimate the PEP according to any one of the above-described embodiments. The PEP estimation circuitry 106 may output the PEP to the user interface or to another signal processing circuitry estimating another parameter using the PEP as an input.

The apparatus may comprise a communication circuitry 102 connected to the processor 100. The communication circuitry may comprise hardware and software suitable for supporting Bluetooth® communication protocol such as Bluetooth Smart specifications. It should be appreciated that other communication protocols are equivalent solutions as long as they are suitable for establishing a personal area network (PAN) or suitable for measurement scenarios described in this document. The processor 100 may use the communication circuitry 102 to transmit and receive frames according to the supported wireless communication protocol. The frames may carry a payload data comprising the above-described measurement data such as ECG measurement data and/or other cardiac measurement data required for the PEP estimation. In some embodiments, the processor 100 may use the communication circuitry 102 to transmit the cardiac measurement data, estimated PEP and/or other parameters to another apparatus, e.g. to a cloud server storing the user's 20 user account.

In an embodiment, the apparatus comprises at least one cardiac activity sensor 120. The heart activity sensor(s) 120 may comprise one or more of the above-described sensors such as an ECG sensor 10, PPG sensor 12, 14, and the BCG sensor 16. Additionally, the apparatus may communicate with at least one cardiac activity sensor 122 through the communication circuitry 102. The at least one heart activity sensor 122 may comprise an external cardiac activity sensor with respect to the apparatus. The cardiac activity sensor(s) 122 may comprise different or different type(s) cardiac activity sensor(s) than the sensor(s) 120. For example, the sensor 120 may include the ECG sensor and one PPG sensor while the sensor 122 is another PPG sensor or a BCG sensor. As another example, the sensor 120 may be a PPG sensor measuring $t_2$ while the ECG sensor and the sensor measuring $t_1$ are external sensors 122.

In embodiments where the cardiac activity sensors are provided in different, physically separate devices, the devices may be synchronized to a common clock such as a clock of Global Positioning System or another satellite navigation system providing an accurate clock signal for both devices. Some wireless communication protocols provide synchronization tools, and some embodiments may use such tools to carry out the synchronization. One of the devices may operate as a master clock and it may transmit a frame indicating its clock value to the other device(s), thereby providing clock synchronization. When the devices have synchronized clocks, a sensor device detecting the blood pulse wave may store a clock value associated with the detection, generate a time stamp representing the clock value, and transmit the time stamp to the other device that uses the time stamp in the computation of the time characteristics of the detected blood pulse wave. The other device may associate the timing indicated by the received time stamp with the closest timing of a detection of the blood pulse wave detected by a cardiac activity sensor comprised in the other device and, as a result, enable PEP estimation on the basis of blood pulse waves detected by the devices synchronously.

The processor 100 may further comprise a test or exercise controller configured to carry out blocks 700 and 702 of FIG. 7. The apparatus may further comprise or be connected to at least one motion sensor configured to monitor the user's motion, as described in connection with FIGS. 5 and 6.

The memory 110 may store a computer program product 118 defining the PEP estimation algorithm the processor executes upon reading the computer program. The memory may further store a user profile 114 of the user 20 storing personal characteristics of the user 20, e.g. age, weight, etc. The memory may further store a measurement database 119 comprising the measured ECG measurement data and the first and second sets of cardiac measurement data for the PEP estimation.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network de-vice, or another network device.

In an embodiment, at least some of the processes described in connection with FIGS. 3 to 7 may be carried out by an apparatus comprising corresponding means for carrying out at least some of the described processes. Some example means for carrying out the processes may include at least one of the following: detector, processor (including dual-core and multiple-core processors), digital signal processor, controller, receiver, transmitter, encoder, decoder, memory, RAM, ROM, software, firmware, display, user interface, display circuitry, user interface circuitry, user interface software, display software, circuit, and circuitry. In an embodiment, the at least one processor 100, the memory 110, and the computer program code 118 form processing means or comprises one or more computer program code portions for carrying out one or more operations according to any one of the embodiments of FIGS. 3 to 8 or operations thereof.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FP-GAs), processors, controllers, micro-controllers, microprocessors, other electronic units designed to perform the functions de-scribed herein, or a combination thereof. For firmware or software, the implementation can be carried out through modules of at least one chipset (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise con-figurations set forth in the given figures, as will be appreciated by one skilled in the art.

Embodiments as described may also be carried out in the form of a computer process defined by a computer program or portions thereof. Embodiments of the methods described in connection with FIGS. 3 to 7 may be carried out by executing at least one portion of a computer program comprising corresponding instructions. The computer program may be in source code form, object code form, or in some intermediate form, and it may be stored in some sort of carrier, which may be any entity or device capable of carrying the pro-gram. For example, the computer program may be stored on a computer pro-gram distribution medium readable by a computer or a processor. The computer program medium may be, for example but not limited to, a record medium, computer memory, read-only memory, electrical carrier signal, telecommunications signal, and software distribution package, for example. The computer program medium may be a non-transitory medium. Coding of software for carrying out the embodiments as shown and described is well within the scope of a per-son of ordinary skill in the art.

It will be obvious to a person skilled in the art that, as the technology advances, the inventive concept can be implemented in various ways. The invention and its embodiments are not limited to the examples described above but may vary within the scope of the claims.

The invention claimed is:

1. A method for estimating a cardiac pre-ejection period of a user, wherein the method is performed by a wearable device worn by the user, the method comprising:

triggering start of a test in the wearable device, the test including cardiac measurements performed on the user while the user takes multiple postures;

instructing, by the wearable device, the user to take a first posture and stay still and measuring, while the user is instructed to stay in the first posture, from the user by using a plurality of cardiac sensor devices, a first subset of electrocardiogram measurement data, a first subset of a first set of cardiac measurement data measured at a first location of the user's body a first distance from the user's heart, and a first subset of a second set of cardiac measurement data measured at a second location of the user's body a second distance from the heart, the second distance different from the first distance;

instructing, by the wearable device, the user to take a second posture different from the first posture and stay still and measuring, while the user is instructed to stay in the second posture, from the user by using the plurality of the cardiac sensor devices, a second subset of the electrocardiogram measurement data, a second subset of the first set of cardiac measurement data measured at the first location of the user's body the first distance from the user's heart, and a second subset of the second set of cardiac measurement data measured at the second location of the user's body the second distance from the heart, wherein the electrocardiogram measurement data is clock-synchronized with the first set of cardiac measurement data and second set of cardiac measurement data;

determining, in the electrocardiogram measurement data, a first set of time instants associated with electric heart activations;

determining, in the first set of cardiac measurement data, a second set of time instants associated with detections of blood pulses at the first location, the blood pulses resulting from the electric heart activations;

determining, in the second set of cardiac measurement data, a third set of time instants associated with detections of the blood pulses at the second location;

forming a set of scatter points on the basis of at least the second set of time instants and the third set of time instants and performing a curve fitting for the scatter points, wherein the scatter points are provided as a function of a time difference between time instants of the second set and time instants of the third set that are associated with a same heart activation, and wherein the curve fitting comprises linear fitting, linear regression, non-linear fitting or non-linear regression; and computing the cardiac pre-ejection period of the user from at least one parameter describing the curve fitting, wherein the at least one parameter is a value of the curve fitting at a point where the time difference is zero, and wherein the cardiac pre-ejection period is computed without knowledge of any distance.

2. The method of claim 1, wherein the parameter is a constant term of the curve fitting.

3. The method of claim 1, wherein the first location and the second location are along a same arterial branch of the user.

4. The method of claim 1, wherein each of the first set of cardiac measurement data and the second set of cardiac measurement data is measured by using a photoplethysmogram sensor or a ballistocardiogram sensor.

5. The method of claim 1, further comprising:

detecting a time interval where the user is sedentary; and limiting the electrocardiogram measurement data and the first and second set of cardiac measurement data to include only cardiac measurement data acquired during the time interval.

6. The method of claim 5, wherein the method is performed by the wearable device worn by the user, the method further comprising:

triggering start of a breathing exercise in the wearable device; and measuring all the electrocardiogram measurement data and the first and second set of cardiac measurement data during the breathing exercise.

7. The method of claim 1, further comprising computing, on the basis of the pre-ejection period, at least one metric indicating a stress level of the user and outputting the at least one metric.

8. A system for estimating a cardiac pre-ejection period of a user, comprising:

an electrocardiogram sensor configured to measure a first subset of electrocardiogram measurement data of the user, while the user is instructed to stay in a first posture, and to measure a second subset of the electrocardiogram measurement data of the user, while the user is instructed to stay in a second posture different from the first posture, a first cardiac sensor configured to measure a first subset of a first set of cardiac measurement data from a first location of the user's body a first distance from the user's heart, while the user is instructed to stay in the first posture, and to measure a second subset of the first set of cardiac measurement data measured at the first location of the user's body the first distance from the user's heart, while the user is instructed to stay in the second posture, a second cardiac sensor configured to measure a first subset of a second set of cardiac measurement data from a second location of the user's body a second distance from the heart, the second distance different from the first distance, while the user is instructed to stay in the first posture, and to measure a second subset of the second set of cardiac measurement data measured at the second location of the user's body the second distance from the heart, while the user is instructed to stay in the second posture, at least one processor, and at least one memory storing a computer program code, wherein the computer program code and the at least one processor are configured to perform operations comprising:

synchronizing the electrocardiogram measurement data with the first set of cardiac measurement data and second set of cardiac measurement data;

determining, in the electrocardiogram measurement data, a first set of time instants associated with heart activations;

determining, in the first set of cardiac measurement data, a second set of time instants associated with detections of blood pulses at the first location, the blood pulses resulting from the heart activations;

determining, in the second set of cardiac measurement data, a third set of time instants associated with detections of the blood pulses at the second location;

forming a set of scatter points on the basis of at least the second set of time instants and the third set of time instants and performing a curve fitting for the scatter points wherein the scatter points are provided as a function of a time difference between time instants of the second set and time instants of the third set that are associated with a same heart activation, and wherein the curve fitting comprises linear fitting, linear regression, non-linear fitting or non-linear regression; and computing the cardiac pre-ejection period of the user from at least one parameter describing the curve fitting, wherein the at least one parameter is a value of the curve fitting at a point where the time difference is zero, and wherein the cardiac pre-ejection period is computed without knowledge of any distance.

9. The system of claim 8, wherein the electrocardiogram sensor, the first cardiac sensor and second cardiac sensor are comprised in or attached to one or more wearable devices, and wherein the electrocardiogram sensor and at least one of the first cardiac sensor and second cardiac sensor are comprised in or attached to a same wearable device.

10. The system of claim 9, wherein the electrocardiogram sensor, the first cardiac sensor and second cardiac sensor are comprised in or attached to a same garment, the garment and the locations of the first cardiac sensor and the second cardiac sensor defining the first location and second location, respectively.

11. The system of claim 9, wherein the electrocardiogram sensor and at least one of the first cardiac sensor and second cardiac sensor are comprised in a wrist-worn training computer, wherein a sensor head of the first cardiac sensor is provided on a face of the training computer that faces the wrist, and wherein the electrocardiogram sensor is provided on a face of the training computer not facing the wrist.

12. A computer program product embodied on a non-transitory distribution medium readable by a computer and comprising program instructions which, when executed by the computer, cause the computer to carry out a computer process comprising:

triggering start of a test in a wearable device worn by a user, the test including cardiac measurements performed on the user while the user takes multiple postures;

instructing the user to take a first posture and stay still and measuring, while the user is instructed to stay in the first posture, from a user by using a plurality of cardiac sensor devices, a first subset of electrocardiogram measurement data, a first subset of a first set of cardiac measurement data measured at a first location of the user's body a first distance from the user's heart, and a first subset of a second set of cardiac measurement data measured at a second location of the user's body a second distance from the heart, the second distance different from the first distance;

instructing the user to take a second posture different from the first posture and stay still and measuring, while the user is instructed to stay in the second posture, from the user by using the plurality of the cardiac sensor devices, a second subset of the electrocardiogram measurement data, a second subset of the first set of cardiac measurement data measured at the first location of the user's body the first distance from the user's heart, and a second subset of the second set of cardiac measurement data measured at the second location of the user's body the second distance from the heart, wherein the electrocardiogram measurement data is clock-synchronized with the first set of cardiac measurement data and second set of cardiac measurement data;

determining, in the electrocardiogram measurement data, a first set of time instants associated with electric heart activations;

determining, in the first set of cardiac measurement data, a second set of time instants associated with detections of blood pulses at the first location, the blood pulses resulting from the electric heart activations;

determining, in the second set of cardiac measurement data, a third set of time instants associated with detections of the blood pulses at the second location;

forming a set of scatter points on the basis of at least the second set of time instants and the third set of time instants and performing a curve fitting for the scatter points, wherein the scatter points are provided as a function of a time difference between time instants of the second set and time instants of the third set that are associated with a same heart activation, and wherein the curve fitting comprises linear fitting, linear regression, non-linear fitting or non-linear regression; and computing a cardiac pre-ejection period of the user from at least one parameter describing the curve fitting, wherein the at least one parameter is a value of the curve fitting at a point where the time difference is zero, and wherein the cardiac pre-ejection period is computed without knowledge of any distance.

* * * * *